(12) United States Patent
Zhou et al.

(10) Patent No.: US 9,298,058 B2
(45) Date of Patent: Mar. 29, 2016

(54) MULTI-STABLE ELECTRONIC INKS

(75) Inventors: Zhang-Lin Zhou, San Diego, CA (US);
Qin Liu, Corvallis, OR (US); Gregg Combs, Monmouth, OR (US); James R. Owen, Salem, OR (US)

(73) Assignee: Hewlett Packard Development Company, L.P., Houston, TX (US)

( * ) Notice: Subject to any disclaimer, the term of this patent is extended or adjusted under 35 U.S.C. 154(b) by 89 days.

(21) Appl. No.: 14/373,363

(22) PCT Filed: Jan. 24, 2012

(86) PCT No.: PCT/US2012/022397
§ 371 (c)(1),
(2), (4) Date: Jul. 20, 2014

(87) PCT Pub. No.: WO2013/112136
PCT Pub. Date: Aug. 1, 2013

(65) Prior Publication Data
US 2014/0376082 A1    Dec. 25, 2014

(51) Int. Cl.
*G02B 26/00* (2006.01)
*G09G 3/34* (2006.01)
(Continued)

(52) U.S. Cl.
CPC .............. *G02F 1/167* (2013.01); *C07D 207/40* (2013.01); *C09D 11/033* (2013.01);
(Continued)

(58) Field of Classification Search
CPC .. C07D 207/40; C07D 277/66; C07D 405/04; C07D 407/04; C09D 11/00; C09D 11/02; C09D 11/033; C09D 11/037; C09D 11/10; C09D 11/34; C09D 11/36; C09D 11/52; G02F 1/0063; G02F 1/0081; G02F 1/167; G02F 2001/1678
USPC ................... 359/296; 345/107; 428/332, 690; 106/31.61, 31.75, 499; 252/301.16; 544/150; 508/547; 442/42
See application file for complete search history.

(56) References Cited

U.S. PATENT DOCUMENTS 6,100,206 A * 8/2000 Scholz .................... A61L 15/12
428/332
6,476,096 B1   11/2002 Molloy et al.
(Continued)

FOREIGN PATENT DOCUMENTS

WO    WO-2009100803    8/2009
WO    WO-2010077238    7/2010
(Continued)

*Primary Examiner* — Loha Ben
(74) *Attorney, Agent, or Firm* — Hewlett-Packard Patent Dept.

(57) ABSTRACT

A compound is disclosed. The compound has the general structure:

wherein Y is selected from the group consisting of hydrocarbons, hydrocarbons including nitrogen in the carbon backbone, and hydrocarbons including oxygen in the carbon backbone; wherein $R_1$ and $R_2$ are each independently selected from the group consisting of hydrogen, linear hydrocarbons, branched hydrocarbons, and cyclic hydrocarbons and wherein $R_1$ and $R_2$ are not both hydrogen; wherein X is selected from the group consisting of $CH_2$, O, N—$R_3$, S, and nothing and wherein $R_3$ is selected from the group consisting of hydrogen, branched hydrocarbons, linear hydrocarbons, and cyclic hydrocarbons; wherein m is an integer between 1 and 50, inclusive; wherein n is an integer between 1 and 10,000, inclusive; and wherein p, q, and z are each independently an integer greater than 0.

15 Claims, 5 Drawing Sheets

(51) Int. Cl.
  *G02F 1/167* (2006.01)
  *C09D 11/52* (2014.01)
  *C07D 207/40* (2006.01)
  *C09D 11/033* (2014.01)
  *C09D 11/037* (2014.01)
  *C09D 11/10* (2014.01)
  *G03G 9/125* (2006.01)
  *G03G 9/135* (2006.01)
  *G02B 1/04* (2006.01)
  *G02F 1/00* (2006.01)
  *C09D 11/34* (2014.01)
  *C09D 11/00* (2014.01)
  *C07D 405/04* (2006.01)

(52) U.S. Cl.
  CPC ............. *C09D 11/037* (2013.01); *C09D 11/10* (2013.01); *C09D 11/52* (2013.01); *G02B 1/04* (2013.01); *G02F 1/0063* (2013.01); *G02F 1/0081* (2013.01); *G03G 9/125* (2013.01); *G03G 9/135* (2013.01); *C07D 405/04* (2013.01); *C09D 11/00* (2013.01); *C09D 11/34* (2013.01); *G02F 2001/1678* (2013.01)

(56) References Cited

U.S. PATENT DOCUMENTS

| | | |
|---|---|---|
| 6,858,070 B1 | 2/2005 | Wong et al. |
| 7,170,670 B2 | 1/2007 | Webber |
| 8,808,878 B2 * | 8/2014 | Hou ..................... C07D 277/66 252/301.16 |
| 2008/0113890 A1 | 5/2008 | Moreton et al. |

FOREIGN PATENT DOCUMENTS

| | | |
|---|---|---|
| WO | WO-2011046562 | 4/2011 |
| WO | WO-2011046563 | 4/2011 |
| WO | WO-2011110221 | 9/2011 |

* cited by examiner

MULTI-STABLE ELECTRONIC INKS

BACKGROUND

Ultrathin, flexible reflective electronic displays that look like print on paper are of great interest as they have potential applications in wearable computer screens, electronic paper, smart identity cards, and electronic signage. Electro-optical display technology, such as electrophoretic or electrokinetic display technology, is an important approach to this type of display medium. In electrophoretic or electrokinetic displays, pixel or segment electrodes, electrodes within the viewing area of a display that are electrically isolated, may control the local position of charged colorant particles in the ink by application of electric fields. The local position of the particles may influence the reflectance of such pixel or segment electrodes. Without subscribing to any particular theory, in electronic inks, particles that exhibit good dispersibility and charge properties in non-polar dispersing media may increase the stability of the ink and may improve the switching behavior of the ink, as further discussed below, which may increase the useful lifetime of the ink. Additionally, use of non-polar dispersing media in the electrophoretic or electrokinetic devices may minimize current leakage.

As noted previously, electrophoretic and electrokinetic displays may have numerous applications. Some display applications, such as e-books and other digital signage applications, do not require updates at the same rate as video display applications. In one example, instead of an update rate measured in fractions of a second, the information displayed in an e-book or another digital signage application may require an update anywhere from every one to two minutes or only once a day. Therefore, if a display does not require constant power to maintain images, it may consume less power when displaying images resulting in power savings and may be more easily remotely deployed.

BRIEF DESCRIPTION OF THE DRAWINGS

The detailed description will make reference to the following drawings, in which like reference numerals may correspond to similar, though perhaps not identical, components. For the sake of brevity, reference numerals having a previously described function may or may not be described in connection with other drawings in which they appear.

DETAILED DESCRIPTION

Figure 1:
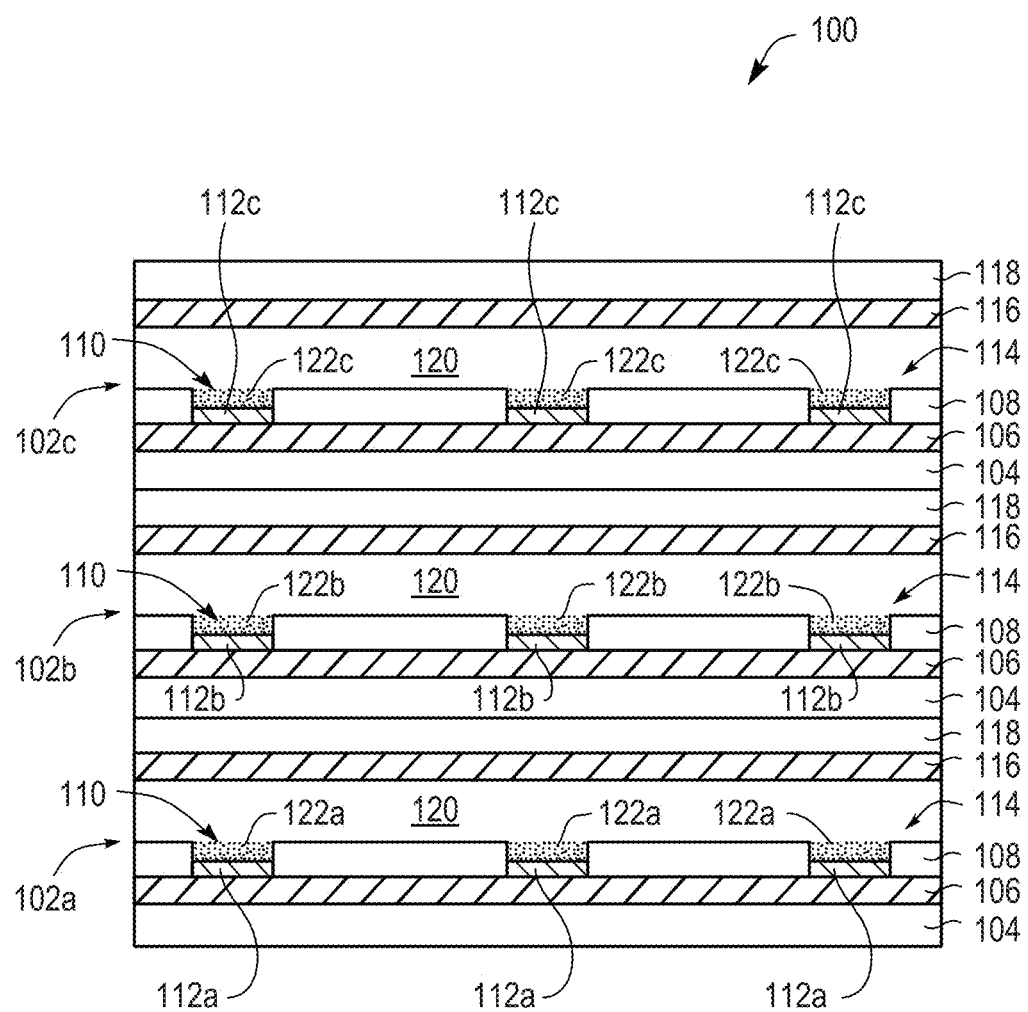
FIG. 1 depicts a cross-sectional view of one example of a stacked electro-optical display including an ink with the amine substituted surfactant disclosed herein.

Reference is now made in detail to specific examples of the disclosed amine substituted surfactant and specific examples of multi-stable electronic inks including such amine substituted surfactants. When applicable, alternative examples are also briefly described.

It is noted that, as used in this specification and the appended claims, the singular forms "a," "an," and "the" include plural referents unless the context clearly dictates otherwise.

As used in this specification and the appended claims, "about" means a ±10% variance caused by, for example, variations in manufacturing processes.

As used herein, the "carrier fluid" is a fluid or medium that fills up a viewing area defined in an electronic ink display and is generally configured as a vehicle to carry colorant particles therein.

Multi-stable or low power reflective color displays or multi-stable displays may be distinguished from traditional displays, such as liquid crystal displays (LCDs), because after a multi-stable display is removed from the power source, the image displayed will remain displayed until power is restored to the device and the image is updated (i.e. changed). "Multi-stability" refers to the ability of the device, after removal from power, to maintain two or more states. As applied to an ink, "multi-stability" refers to the ability of the ink to do the same. In multi-stable devices capable of two states, such states appear on the device as a maximum color-saturated state, sometimes known as the "dark state" and a minimum color-saturated state, sometimes known as the "clear state" and wherein the minimum level of saturation is determined by the specifications of the device. In multi-stable devices including more than two states, there may be one or more additional different colored states, each state independently having a different level of color saturation between the maximum color-saturated state and the minimum color-saturated state.

Accordingly, multi-stable or low power displays may be desirable in applications such as e-book readers and signage applications that may not require as many image updates as a video display. For example, often, an active display may be the largest power-consuming component in a portable device. Therefore, in some portable devices, such as e-books or other signage displays where images may remain static for long periods of time, use of multi-stable displays may allow power to be turned off and conserved during such static times, which may result in a device with a longer battery life.

In one example, a multi-stable display may be an electrokinetic device that includes multi-stable inks. Such a display, as discussed above, may require only the power necessary to change the image displayed, with no additional power required to maintain the image. In contrast, electrokinetic displays using other inks, such as non-multi-stable inks, may require complex driving schemes for maintaining gray scale control and the static images, which may require more power. Additionally, use of multi-stable inks may allow for the use of passive matrix devices that use patterned electrodes in the viewing area instead of active matrix devices that use more complicated transistors at each pixel, which may reduce manufacturing complexity and costs. Therefore, using multi-stable electronic inks in electrokinetic devices may result in devices with simplified driving schemes and low power consumption, which may result in power savings and devices with a longer battery life.

However, multi-stable inks may be difficult to create as the mechanisms for multi-stability are not well understood. For example, current commercial multi-stable displays, such as displays manufactured by prior art display technology companies, utilize front to rear particle motion, which may only be able to provide opaque color and white states or black and white states. Additionally, such displays may not be capable of producing the clear states that allow displays to be used in stacked architectures, as further described below, and may rely on color filters to achieve full color. However, color filters, such as red, green, and blue filters, may often be arranged side-by-side in a pixel, which may result in a decreased surface area within the pixel for modulating light and a decreased surface area within the pixel for reflecting incident light when not all of the color filters are required to produce a color. Accordingly, the resulting displayed image may have duller colors.

The ability to achieve a clear state, on the other hand and as further described below, allows displays to sit in a stacked architecture, which allows the entire viewable area in the display to be used (i.e. the entire pixel of every pixel) when modulating light and reflecting incident light, which may result in the display achieving brighter colors and a better light state. Additionally, because the entire viewable area in the display may be used to modulate light, such displays may also have a larger color gamut volume.

In the past, Hewlett-Packard has researched displays utilizing electrokinetic architecture that rely on pigment compaction, which permits both a colored state when the colorant particles are spread out and a clear state when the particles are tightly compacted within a cell or pixel, and wherein the repeated motion of spreading out and compacting is known as "switching". (See e.g., Yeo. J. et al., "Electro-optical Display" patented as U.S. Pat. No. 8,018,642). However, inks currently used in prior art displays may not work in an electrokinetic architecture as such inks may be unable to achieve the level of compaction necessary to provide the clear states necessary in displays with stacked color architectures, as further described below. Accordingly, researchers continue to develop electronic inks for such stacked architectures by researching and improving the conventional stabilization techniques and materials used in multi-stable inks. (See e.g., Zhou. Z. L. et al., "Electronic Inks" published on Apr. 21, 2011 as WO2011/046562; Zhou, Z. L. et al., "Dual Color Electronically Addressable Ink" published on Apr. 21, 2011 as WO2011/046564; and Zhou, Z. L. et al., "Electronic Inks" published on Apr. 21, 2011 as WO2011/046563.)

A new multi-stable electronic ink for low power electrophoretic displays is disclosed, wherein the new multi-stable electronic ink includes a new surfactant including polyisobutylene chains that may serve as a hydrophobic tail and a linear, branched, or cyclic hydrocarbon substituted tertiary amine that may serve as a hydrophilic head. The new surfactants disclosed herein are derived by replacing the terminal primary amine groups in conventional surfactant molecules with linear, branched, or cyclic hydrocarbon substituted tertiary amines. Without subscribing to any particular theory, there may be several contributing factors to why such surfactants may cause electronic inks to have multi-stability properties. First, because these surfactants may have larger polar head groups and may be less hydrophilic, the surfactants may exhibit more steric stabilization due to greater steric hindrance of the one or more alkyl groups on the end of the surfactant, which may prevent particles from agglomerating.

Additionally, the nitrogen atom at the terminal end of the surfactant molecule may be more electron rich due to the electron-donating nature of the one or more alkyl groups, which in turn, may make acid-base reactions easier to achieve. Acid-base reactions between the pigment surface and a surfactant may comprise one mechanism for charging pigment particles.

FIG. 1 illustrates a cross-sectional view of one example of a stacked electro-optical display 100 including an ink with the amine substituted surfactant disclosed herein. The electro-optical display 100 includes a first display element 102a, a second display element 102b, and a third display element 102c. The third display element 102c is stacked on the second display element 102b, and the second display element 102b is stacked on the first display element 102a. Turning now to electronic inks 120, 122 that employ the surfactants disclosed herein, examples of such electronic inks may generally include a non-polar carrier fluid 120, a pigment particle 122, the surfactant disclosed herein, and other additives, such as other surfactants, dispersants or charge directors.

Each display unit includes a first substrate 104, a first electrode 106, a dielectric layer 108 including reservoir or recess regions 110, thin layers 112, a display cell 114, a second electrode 116, and a second substrate 118. The display cell 114 may be filled with the electronic ink disclosed herein including a carrier fluid 120 including colorant particles 122. In some examples, the thin layers 112 may be opaque. In other examples, the thin layers 112 may be transparent.

The first display element 102a includes thin layers 112a self-aligned within the recess regions 110. The first display element 102a also includes colorant particles 122a having a first color (e.g., cyan) for a full color electro-optical display. The second display element 102b includes thin layers 112b self-aligned within the recess regions 110. The second display element 102b also includes colorant particles 122b having a second color (e.g., magenta) for a full color electro-optical display. The third display element 102c includes thin layers 112c self-aligned within the recess regions 110. The third display element 102c also includes colorant particles 122c having a third color (e.g., yellow) for a full color electro-optical display. In other examples, colorant particles 122a, 122b, and 122c may include other suitable colors for providing an additive or subtractive full color electro-optical display.

In the example illustrated in FIG. 1, in the electro-optical display 100 including the electronic ink disclosed herein 120, 122, the first display element 102a, the second display element 102b, and the third display element 102c are aligned with each other. As such, the thin layers 112a, 112b, and 112c are also aligned with each other. In this example, since the recess regions 110 and the self-aligned thin layers 112a, 112b, and 112c of each display element 102a, 102b, and 102c, respectively, are aligned, the clear aperture for the stacked electro-optical display 100 may be improved as compared to a stacked electro-optical display without such alignment.

In an alternate example (not shown), the first display element 102a, the second display element 102b, and the third display element 102c may be offset from each other. As such, the thin layers 112a, 112b, and 112c are also offset from each other. In this example, since the recess regions 110 and the self-aligned thin layers 112a, 112b, and 112c are just a fraction of the total area of each display element 102a, 102b, and 102c, respectively, the clear aperture for the stacked electro-optical display 100 may remain high regardless of the alignment between the display elements 102a, 102b, and 102c. As such, the process for fabricating the stacked electro-optical display 100 may be simplified. The self-aligned thin layers 112a, 112b, and 112c may prevent tinting of each display element due to the colorant particles 122a, 122b, and 122c, respectively, in the clear optical state. Therefore, a stacked full color electro-optical display having a bright, neutral clear state and precise color control may be provided.

As briefly discussed above, in some examples, electronic inks used in such electro-optical displays, such as electrokinetic displays, may include a carrier fluid 120, a colorant particle 122, and other additives, such as, but not limited to, surfactants, dispersants, and charge directors. When used in an electronic ink, in some examples, surfactants may be colorless molecules that are dispersible or soluble in the carrier fluid of the electronic ink. In some examples, a surfactant may be present directly on the surface of a pigment particle or on a resin particle that contains a pigment. In such examples, the surfactant may create charge on the pigment or colorant particles, may carry counter charges that stabilize the ink, or may help prevent colorant particle aggregation.

In the past, small molecules or polymers that may be capable of forming reverse micelles in non-polar solvents have been used as surfactants in electronic inks. Examples include, but are not limited to, neutral and non-dissociable charge director such as polyisobutylene succinimide amines; the Chevron Oronite dispersant, an example of which is depicted below:

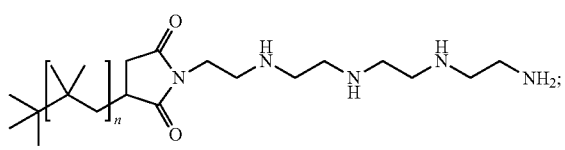

(1)

ionizable charge directors that may disassociate to form charges such as sodium di-2-ethylhexylsulfosuccinate dioctyl sulfosuccinate (AOT), as depicted below:

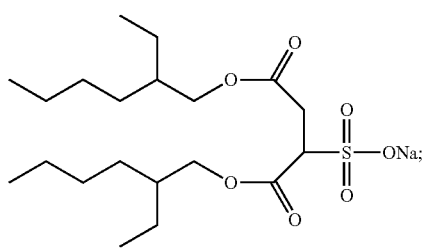

(2)

zwitterionic charge director such as Lecithin, as depicted below:

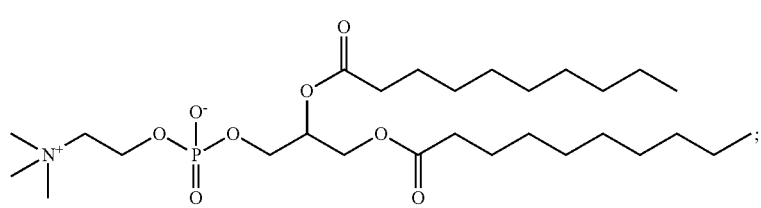

(3)

and non-chargeable and neutral charge directors, which may not disassociate or react with acids or bases to form charges such as fluorosurfactants, an example of which is depicted below:

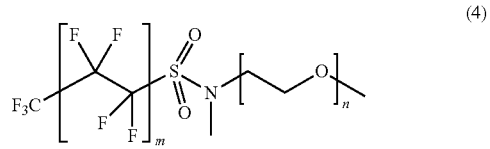

(4)

However, while electronic inks including the surfactants described above may have reasonable switching properties, in multi-stable electronic ink applications, such surfactants may not demonstrate reliable multi-stable properties.

As discussed above, a new surfactant is disclosed, wherein such surfactants may be derived by replacing the terminal primary amine groups in conventional surfactant molecules with hydrocarbon substituted tertiary amines. In one example, a general structure for a surfactant including a linear or branched hydrocarbon substituted tertiary amine may be:

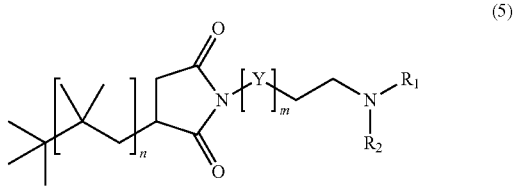

(5)

wherein Y is selected from the group consisting of hydrocarbons, hydrocarbons including nitrogen in the carbon backbone, and hydrocarbons including oxygen in the carbon backbone; wherein m is an integer between 1 and 5, inclusive; wherein $R_1$ and $R_2$ are each independently selected from the group consisting of hydrogen, branched hydrocarbons, linear hydrocarbons, and cyclic hydrocarbons, such as alkyls, alkenyls, aryls, arylalkyls, or cycloalkanealkyls and wherein $R_1$ and $R_2$ are not both hydrogen; wherein m is an integer between 1 and 50, inclusive; and wherein n is an integer between 1 and 10,000, inclusive. In some specific non-limiting examples, Y may be an aliphatic amine, ethylene, ethylene glycol, propylene, isopropyl, or other hydrocarbons including between 1 and 50 carbons, inclusive, such as alkyls, alkenyls, aryls, arylalkyls or cycloalkanealkyls. Furthermore, in some examples, one of Y, $R_1$, and $R_2$ may the same or may be different from another one of Y, $R_1$, and $R_2$; likewise, m and n may be the same or may be different from one another.

In another example, a general structure for a surfactant including a cyclic hydrocarbon substituted tertiary amine may be:

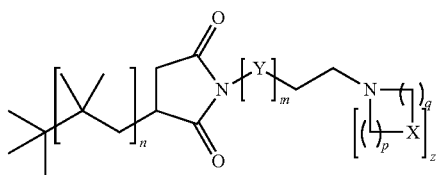

(6)

wherein Y is selected from the group consisting of hydrocarbons, hydrocarbons including nitrogen in the carbon backbone, and hydrocarbons including oxygen in the carbon backbone; wherein X is selected from the group consisting of $CH_2$, O, N—$R_3$, S, or nothing, wherein "C" is carbon, "O" is oxygen, "N" is nitrogen, "H" is hydrogen, and "S" is sulfur and wherein $R_3$ is selected from the group consisting of hydrogen, branched hydrocarbons, linear hydrocarbons, and cyclic hydrocarbons, such as alkyls, alkenyls, aryls, arylalkyls, or cycloalkanealkyls; wherein p, q, and z are each independently any integer greater than or equal to 1; wherein m is any integer between 1 and 50, inclusive; and wherein n is any integer between 1 and 10,000, inclusive. In some specific non-limiting examples, Y may be an aliphatic amine, ethylene, ethylene glycol, propylene, isopropyl, or any other hydrocarbon including between 1 and 50 carbons, inclusive, such as alkyls, alkenyls, aryls, arylalkyls, or cycloalkanealkyls. In other examples, Y may be any hydrocarbon, any hydrocarbon including nitrogen in the carbon backbone or any hydrocarbon including oxygen in the carbon backbone. Furthermore, in some examples, one of m, n, p, q, and z may be the same or may be different from another one of m, n, p, q, and z.

As used herein, when X is nothing in a surfactant including a cyclic hydrocarbon substituted tertiary amine, as described in the previous paragraph, there is a bond between the $(C)_p$ and $(C)_q$, an example of which is illustrated below in (7):

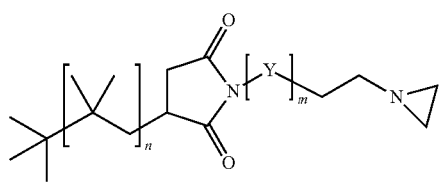

(7)

wherein Y, m, and n have the same values and characteristics as Y, m, and n in the general structures for the surfactant disclosed herein as (5) and (6).

In one specific example, wherein p and q are 1 and z is 2 in the general structure for the surfactant including a cyclic hydrocarbon substituted tertiary amine, the surfactant structure is as illustrated below in (8):

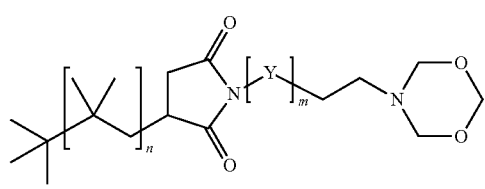

(8)

wherein Y, m, and n have the same values and characteristics as Y, m, and n in the general structures for the surfactant disclosed herein as (5) and (6).

Two specific examples of surfactants disclosed herein, wherein Y is an aliphatic amine, may be depicted as (9) and (10) below:

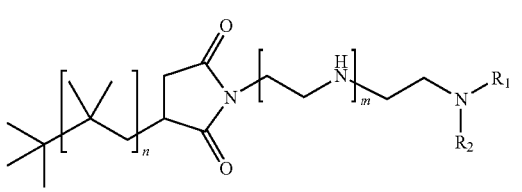

(9)

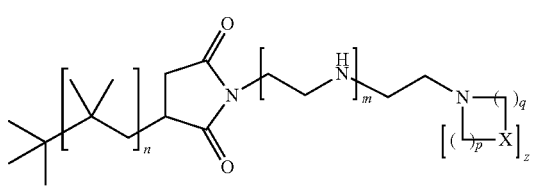

(10)

wherein $R_1$ and $R_2$ are each independently selected from the group consisting of hydrogen and hydrocarbons, such as alkyls, alkenyls, aryls, arylalkyls, or cycloalkanealkyls and wherein $R_1$ and $R_2$ are not both hydrogen; wherein X is selected from the group consisting of $CH_2$, O, N—$R_3$, S, or nothing and wherein $R_3$ is selected from the group consisting of hydrogen, branched hydrocarbons, linear hydrocarbons, and cyclic hydrocarbons such as alkyls, alkenyls, aryls, arylalkyls, or cycloalkanealkyls; wherein m is an integer between 1 and 50, inclusive; wherein n is an integer between 1 and 10,000, inclusive; and wherein p, q and z are each independently an integer greater than or equal to 1. In some examples, $R_1$ and $R_2$ may the same or may be different from one another, and m and n may be the same or may be different from one another. Likewise, one of m, n, p, q, and z may be the same or may be different as another one of m, n, p, q, and z.

Specific examples of surfactants, wherein Y is an aliphatic amine, further including an alkyl substituted tertiary amine terminated aliphatic amine may include but are not limited to:

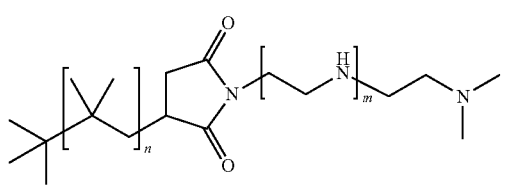

(11)

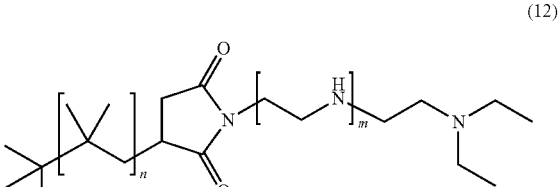

(12)

(13)

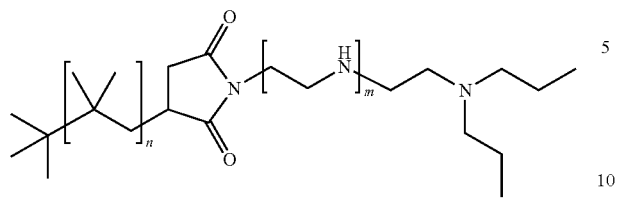

(14)

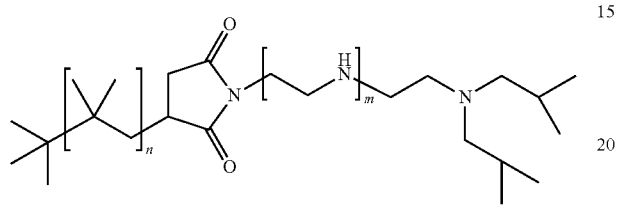

wherein m and n have the same values and characteristics as the m and n in the structures of the surfactant wherein Y is an aliphatic amine disclosed herein as (9) and (10).

Specific examples of surfactants, wherein Y is an aliphatic amine, further including a cycloalkyl substituted tertiary amine terminated aliphatic amine may include but are not limited to:

(15)

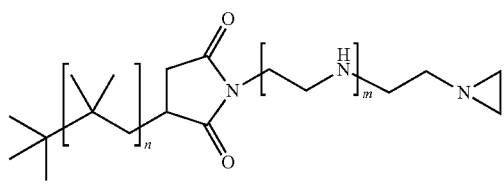

(16)

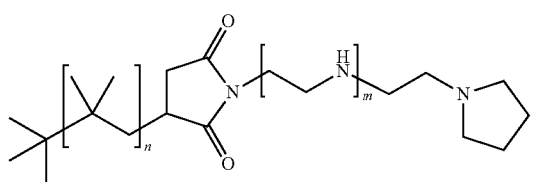

(17)

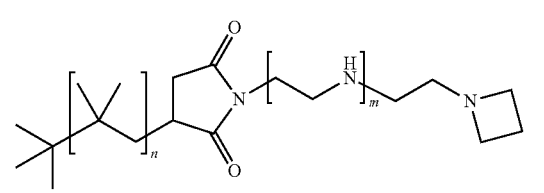

(18)

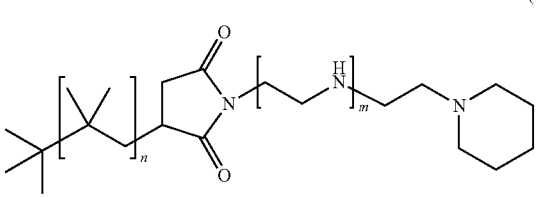

(19)

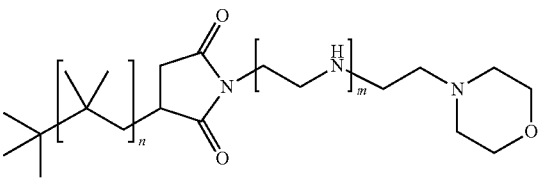

wherein m and n have the same values and characteristics as the m and n in the structures of the surfactant wherein Y is an aliphatic amine disclosed herein as (9) and (10).

Two specific examples of surfactants disclosed herein, wherein Y is ethylene glycol, may be depicted as (20) and (21) below:

(20)

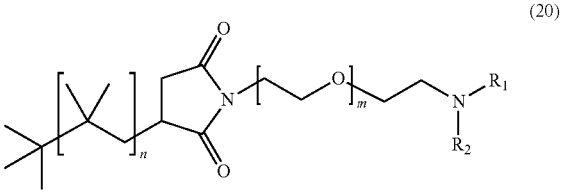

(21)

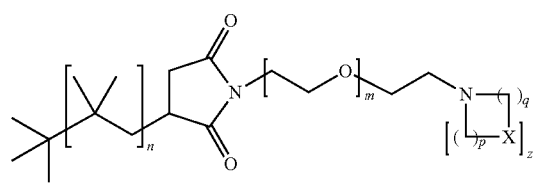

wherein $R_1$, $R_2$, X, m, n, p, q, and z have the same values and characteristics as the $R_1$, $R_2$, X, m, n, p, q, and z in the structures for the surfactant wherein Y is an aliphatic amine disclosed herein as (9) and (10).

Specific examples of surfactants including an alkyl substituted tertiary amine terminated ethylene glycol may include but are not limited to:

(22)

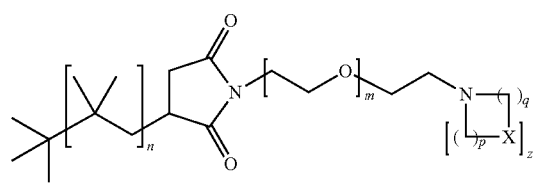

(23)

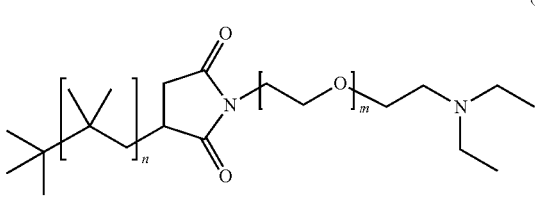

(24)

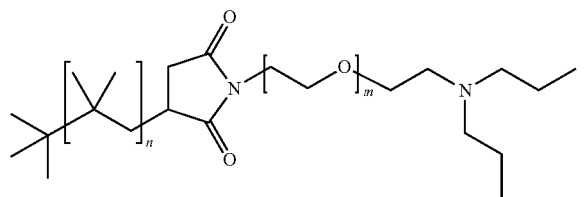

(25)

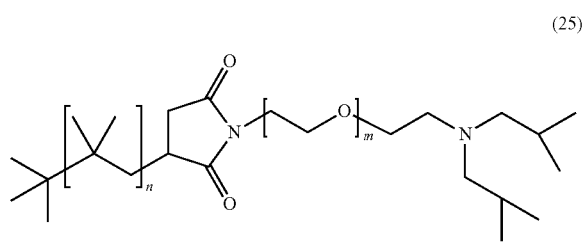

wherein m and n have the same values and characteristics as the m and n in the structures of the surfactant wherein Y is an aliphatic amine disclosed herein as (9) and (10).

Specific examples of surfactants including an cycloalkyl substituted tertiary amine terminated ethylene glycol may include but are not limited to:

(26)

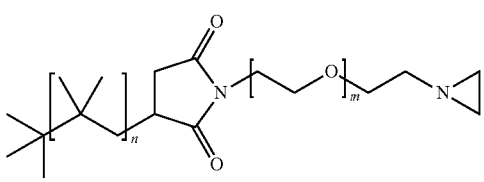

(27)

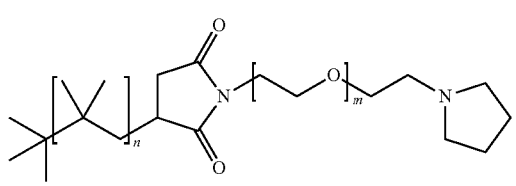

(28)

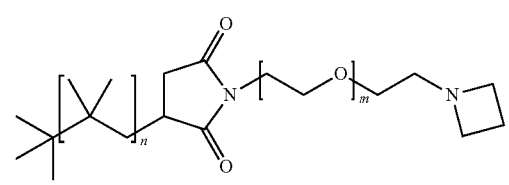

(29)

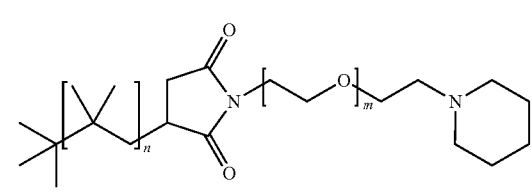

(30)

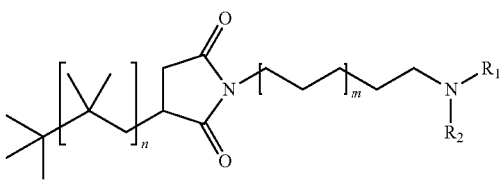

wherein m and n have the same values and characteristics as the m and n in the structures for the surfactant wherein Y is an aliphatic amine disclosed herein as (9) and (10).

Two specific examples of surfactants disclosed herein, wherein Y is an alkane, may be depicted as (31) and (32) below:

(31)

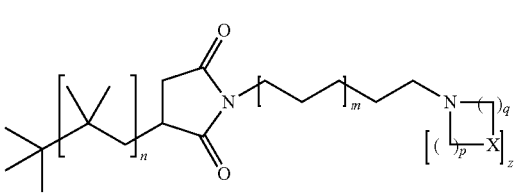

(32)

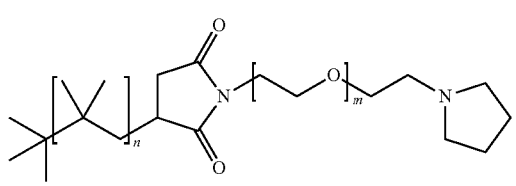

wherein $R_1$, $R_2$, X, m, n, p, q, and z have the same values and characteristics as the $R_1$, $R_2$, X, m, n, p, q, and z in the structures for the surfactant wherein Y is an aliphatic amine disclosed herein as (9) and (10).

Specific examples of surfactants including an alkyl substituted tertiary amine terminated alkane may include but are not limited to:

(33)

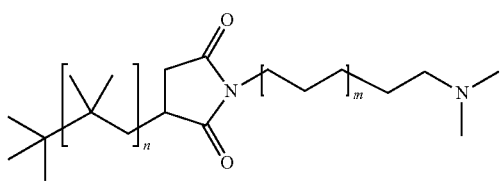

(34)

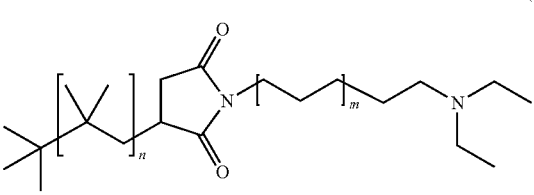

(35)
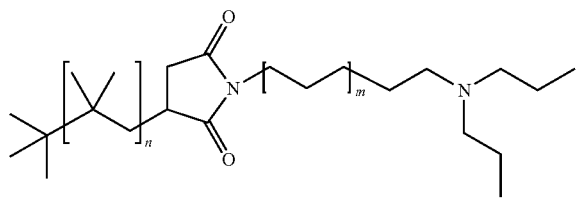

(36)
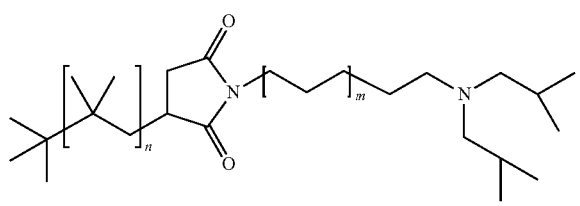

wherein m and n have the same values and characteristics as the m and n in the structures for the surfactants wherein Y is an aliphatic amine disclosed herein as (9) and (10).

Specific examples of surfactants including a cycloalkyl substituted tertiary amine terminated alkane may include but are not limited to:

(37)
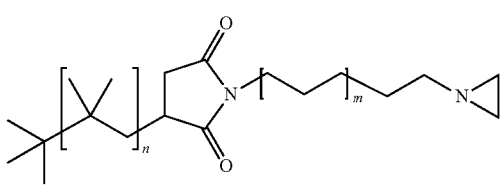

(38)
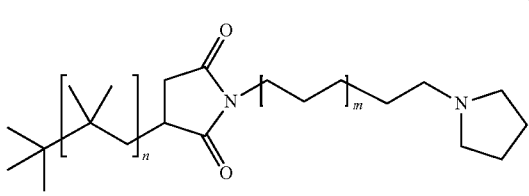

(39)
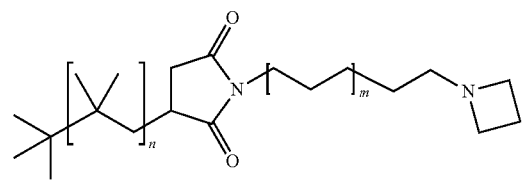

(40)
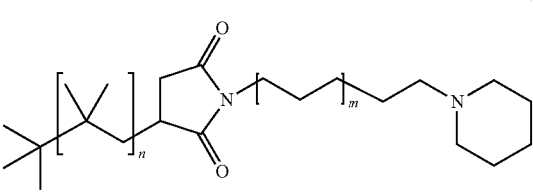

(41)
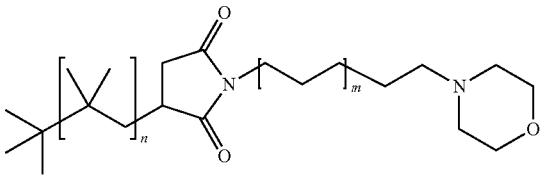

wherein m and n have the same values and characteristics as the m and n in the structures for the surfactants wherein Y is an aliphatic amine disclosed herein as (9) and (10).

Turning now to electronic inks that employ the surfactants disclosed herein, examples of such electronic inks may generally include a non-polar carrier fluid, a pigment particle, the surfactant disclosed herein, and other additives, such as other surfactants, dispersants or charge directors.

In some examples, the carrier fluid may act as a vehicle for dispersing the pigment particle and may act as an electrokinetic or electrophoretic medium. In one example, non-polar fluids are used, as such fluids may reduce leakages of electric current when driving the display and may increase the electric field present in the ink. In some examples, the non-polar carrier fluid may be a fluid having a low dielectric constant k such as, e.g., less than about 20 or, in some examples, less than about 2. In response to a sufficient electric potential or field applied to the colorant particles while driving electrodes in the display, the colorant particles may move or rotate to different spots in the area of the display viewable by a user to produce different images. In other examples, carrier fluids may also vary with respect to viscosity, resistivity, specific gravity, chemical stability, or toxicity, and in other examples, such differences may be considered when formulating an electronic ink. For example, a carrier fluid that is too viscous may slow down the spread or compaction of the colorant particles, which may affect the switching speed and may result in a less effective electronic ink.

Specifically, in some examples, the non-polar carrier fluid may include one or more fluids selected from the group consisting of hydrocarbons, halogenated hydrocarbons, partially halogenated hydrocarbons, oxygenated fluids, siloxanes, and combinations thereof. Some specific examples of non-polar carrier fluids may include, but are not limited to, perchloroethylene, cyclohexane, dodecane, mineral oil, isoparaffinic fluids, cyclopentasiloxane, cyclohexasiloxane, cyclooctamethylsiloxane or combinations thereof.

In some examples, pigment or colorant particle added to electronic inks may provide color and charge to the electronic ink. Similar to the carrier fluid in the ink, different pigment or colorant particles may have different characteristics, such as different sizes, dispersibility properties, hues, colors, or lightness. Additionally, different pigment particles may be further functionalized to contain different functional groups, which may further vary properties of the particle, including, but not limited to, hydrophilicity and hydrophobicity, acidity and basicity, or density of the particles.

The pigment particle may be a colored pigment or colored polymeric particle in any possible color, such as RGB or CYMK, with a size ranging from 10 nm to 10 µm. In some examples, smaller particles, with a particle size from 1 to 10 nm, such as quantum dots, may be employed. In other examples, the particle size may range to a few micrometers. Additionally, organic or inorganic pigments may be used.

Organic and inorganic pigment particles may be selected from black pigment particles, yellow pigment particles, magenta pigment particles, red pigment particles, violet pigment particles, cyan pigment particles, blue pigment particles, green pigment particles, orange pigment particles, brown pigment particles or white pigment particles. In some instances, the organic or inorganic pigment particles may include spot-color pigment particles, which are formed from a combination of a predefined ratio of two or more primary color pigment particles.

A non-limiting example of a suitable inorganic black pigment includes carbon black. Examples of carbon black pigments include those manufactured by Mitsubishi Chemical Corporation, Japan (such as, e.g., carbon black No. 2300, No. 900, MCF88, No. 33, No. 40, No. 45, No. 52, MA7, MA8, MA100 or No. 0B); various carbon black pigments of the RAVEN® series manufactured by Columbian Chemicals Company, Marietta, Ga., (such as, e.g., RAVEN® 5750, RAVEN® 5250, RAVEN® 5000, RAVEN® 3500, RAVEN® 1255 or RAVEN® 700); various carbon black pigments of the REGAL® series, the MOGUL® series or the MONARCH® series manufactured by Cabot Corporation, Boston, Mass., (such as, e.g., REGAL® 400R, REGAL® 330R, REGAL® 660R, MOGUL® L, MONARCH® 700, MONARCH® 800, MONARCH® 880, MONARCH® 900, MONARCH® 1000, MONARCH® 1100, MONARCH® 1300 or MONARCH® 1400); or various black pigments manufactured by Evonik Degussa Corporation, Parsippany, N.J., (such as, e.g., Color Black FW1, Color Black FW2, Color Black FW2V, Color Black FW18, Color Black FW200, Color Black S150, Color Black S160, Color Black S170, PRINTEX® 35, PRINTEX® U, PRINTEX® V, PRINTEX® 140U, Special Black 5, Special Black 4A or Special Black 4). A non-limiting example of an organic black pigment includes aniline black, such as C.I. Pigment Black 1.

Other examples of inorganic pigments include metal oxides and ceramics, such as the oxides of iron, zinc, cobalt, manganese or nickel. Non-limiting examples of suitable inorganic pigments include those from the Shepherd Color Company (Cincinnati, Ohio) such as Black 10C909A, Black 10P922, Black 1G, Black 20F944, Black 30C933, Black 30C940, Black 30C965, Black 376A, Black 40P925, Black 411A, Black 430, Black 444, Blue 10F545, Blue 10G511, Blue 10G551, Blue 10K525, Blue 10K579, Blue 211, Blue 212, Blue 214, Blue 30C527, Blue 30C588, Blue 30C591, Blue 385, Blue 40P585, Blue 424, Brown 10C873, Brown 10P835, Brown 10P850, Brown 10P857, Brown 157, Brown 20C819, Green 10K637, Green 187B, Green 223, Green 260, Green 30C612, Green 30C654, Green 30C678, Green 40P601, Green 410, Orange 10P320, StarLight FL 37, StarLight FL105. StarLight FL500, Violet 11, Violet 11C, Violet 92, Yellow 10C112, Yellow 10C242, Yellow 10C272, Yellow 10P110, Yellow 10P225, Yellow 10P270, Yellow 196, Yellow 20P296, Yellow 30C119, Yellow 30C236, Yellow 40P140 or Yellow 40P280.

The following is a list of organic pigments that may be treated in accordance with the teachings herein. Non-limiting examples of suitable yellow pigments include C.I. Pigment Yellow 1, C.I. Pigment Yellow 2, C.I. Pigment Yellow 3, C.I. Pigment Yellow 4, C.I. Pigment Yellow 5, C.I. Pigment Yellow 6, C.I. Pigment Yellow 7, C.I. Pigment Yellow 10, C.I. Pigment Yellow 11, C.I. Pigment Yellow 12, C.I. Pigment Yellow 13, C.I. Pigment Yellow 14, C.I. Pigment Yellow 16, C.I. Pigment Yellow 17, C.I. Pigment Yellow 24, C.I. Pigment Yellow 34, C.I. Pigment Yellow 35. C.I. Pigment Yellow 37, C.I. Pigment Yellow 53. C.I. Pigment Yellow 55, C.I. Pigment Yellow 65, C.I. Pigment Yellow 73, C.I. Pigment Yellow 74, C.I. Pigment Yellow 75, C.I. Pigment Yellow 81, C.I. Pigment Yellow 83, C.I. Pigment Yellow 93, C.I. Pigment Yellow 94. C.I. Pigment Yellow 95, C.I. Pigment Yellow 97, C.I. Pigment Yellow 98, C.I. Pigment Yellow 99, C.I. Pigment Yellow 108, C.I. Pigment Yellow 109, C.I. Pigment Yellow 110, C.I. Pigment Yellow 113, C.I. Pigment Yellow 114, C.I. Pigment Yellow 117, C.I. Pigment Yellow 120, C.I. Pigment Yellow 124, C.I. Pigment Yellow 128, C.I. Pigment Yellow 129, C.I. Pigment Yellow 133, C.I. Pigment Yellow 138, C.I. Pigment Yellow 139, C.I. Pigment Yellow 147, C.I. Pigment Yellow 151, C.I. Pigment Yellow 153, C.I. Pigment Yellow 154, Pigment Yellow 155, C.I. Pigment Yellow 167, C.I. Pigment Yellow 172 or C.I. Pigment Yellow 180.

Non-limiting examples of suitable magenta or red or violet organic pigments include C.I. Pigment Red 1, C.I. Pigment Red 2, C.I. Pigment Red 3, C.I. Pigment Red 4, C.I. Pigment Red 5, C.I. Pigment Red 6, C.I. Pigment Red 7, C.I. Pigment Red 8, C.I. Pigment Red 9, C.I. Pigment Red 10, C.I. Pigment Red 11, C.I. Pigment Red 12, C.I. Pigment Red 14, C.I. Pigment Red 15, C.I. Pigment Red 16, C.I. Pigment Red 17, C.I. Pigment Red 18, C.I. Pigment Red 19, C.I. Pigment Red 21, C.I. Pigment Red 22, C.I. Pigment Red 23, C.I. Pigment Red 30, C.I. Pigment Red 31, C.I. Pigment Red 32, C.I. Pigment Red 37, C.I. Pigment Red 38, C.I. Pigment Red 40, C.I. Pigment Red 41, C.I. Pigment Red 42, C.I. Pigment Red 48(Ca), C.I. Pigment Red 48(Mn), C.I. Pigment Red 57(Ca), C.I. Pigment Red 57:1, C.I. Pigment Red 88, C.I. Pigment Red 112, C.I. Pigment Red 114, C.I. Pigment Red 122, C.I. Pigment Red 123, C.I. Pigment Red 144, C.I. Pigment Red 146, C.I. Pigment Red 149, C.I. Pigment Red 150, C.I. Pigment Red 166, C.I. Pigment Red 168, C.I. Pigment Red 170, C.I. Pigment Red 171, C.I. Pigment Red 175, C.I. Pigment Red 176, C.I. Pigment Red 177, C.I. Pigment Red 178, C.I. Pigment Red 179, C.I. Pigment Red 184, C.I. Pigment Red 185, C.I. Pigment Red 187, C.I. Pigment Red 202, C.I. Pigment Red 209, C.I. Pigment Red 219, C.I. Pigment Red 224, C.I. Pigment Red 245, C.I. Pigment Violet 19, C.I. Pigment Violet 23, C.I. Pigment Violet 32, C.I. Pigment Violet 33, C.I. Pigment Violet 36, C.I. Pigment Violet 38, C.I. Pigment Violet 43 or C.I. Pigment Violet 50.

Non-limiting examples of blue or cyan organic pigments include C.I. Pigment Blue 1, C.I. Pigment Blue 2, C.I. Pigment Blue 3, C.I. Pigment Blue 15, C.I. Pigment Blue 15:3. C.I. Pigment Blue 15:34, C.I. Pigment Blue 15:4, C.I. Pigment Blue 16, C.I. Pigment Blue 18, C.I. Pigment Blue 22, C.I. Pigment Blue 25, C.I. Pigment Blue 60, C.I. Pigment Blue 65, C.I. Pigment Blue 66, C.I. Vat Blue 4 or C.I. Vat Blue 60.

Non-limiting examples of green organic pigments include C.I. Pigment Green 1, C.I. Pigment Green 2, C.I. Pigment Green 4, C.I. Pigment Green 7, C.I. Pigment Green 8, C.I. Pigment Green 10, C.I. Pigment Green 36 or C.I. Pigment Green 45.

Non-limiting examples of brown organic pigments include C.I. Pigment Brown 1, C.I. Pigment Brown 5, C.I. Pigment Brown 22, C.I. Pigment Brown 23, C.I. Pigment Brown 25, and C.I. Pigment Brown, C.I. Pigment Brown 41 or C.I. Pigment Brown 42.

Non-limiting examples of orange organic pigments include C.I. Pigment Orange 1, C.I. Pigment Orange 2, C.I. Pigment Orange 5, C.I. Pigment Orange 7, C.I. Pigment Orange 13, C.I. Pigment Orange 15, C.I. Pigment Orange 16, C.I. Pigment Orange 17, C.I. Pigment Orange 19, C.I. Pigment Orange 24, C.I. Pigment Orange 34, C.I. Pigment Orange 36, C.I. Pigment Orange 38, C.I. Pigment Orange 40, C.I. Pigment Orange 43 or C.I. Pigment Orange 66.

In some examples, colorant particles may be dispersed in the carrier fluid. In one example, the colorant particles may be selected from pigment particles that are self-dispersible in the non-polar carrier fluid. It is to be understood, however, that non-dispersible pigment particles may otherwise be used so long as the electronic ink includes one or more suitable dispersants. Such dispersants include hyperdispersants such as those of the SOLSPERSE® series manufactured by Lubrizol Corp., Wickliffe, Ohio (e.g., SOLSPERSE® 3000, SOLSPERSE® 8000, SOLSPERSE® 9000, SOLSPERSE® 11200, SOLSPERSE® 13840, SOLSPERSE® 16000, SOLSPERSE® 17000, SOLSPERSE® 18000, SOLSPERSE® 19000, SOLSPERSE® 21000 or SOLSPERSE® 27000); various dispersants manufactured by BYKchemie, Gmbh, Germany, (e.g., DISPERBYK® 110, DISPERBYK® 163, DISPERBYK® 170 or DISPERBYK® 180); various dispersants manufactured by Evonik Goldschmidt GMBH LLC, Germany, (e.g., TEGO® 630, TEGO® 650, TEGO® 651, TEGO® 655, TEGO® 685 or TEGO® 1000); or various dispersants manufactured by Sigma-Aldrich, St. Louis, Mo., (e.g., SPAN® 20, SPAN® 60, SPAN® 80 or SPAN® 85).

Finally, in some examples, the electronic ink may further include other additives such as charge directors that may further facilitate the charging of colorant particles. In one example, the charge director may be basic and may react with the acid-modified colorant particle to negatively charge the particle. In other words, the charging of the particle may be accomplished via an acid-base reaction (or interaction) between the charge director and the acid-modified particle surface. It is to be understood that the charge director may also be used in the electronic ink to prevent undesirable aggregation of the colorant in the carrier fluid. In other examples, the charge director may be acidic and may react (or interact) with the base-modified colorant particle to positively charge the particle. Again, the charging of the particle may be accomplished via an acid-base reaction (or interaction) between the charge director and the base-modified particle surface.

The charge director may be selected from small molecules or polymers that may be capable of forming reverse micelles in the non-polar carrier fluid. Such charge directors may be colorless and may be dispersible or soluble in the carrier fluid. As discussed above, examples of charge directors include, but are not limited to, neutral and non-dissociable charge director such as polyisobutylene succinimide amines: the Chevron Oronite dispersant, ionizable charge directors that may disassociate to form charges such as sodium di-2-ethylhexylsulfosuccinate dioctyl sulfosuccinate (AOT), zwitterionic charge director such as Lecithin, and non-chargeable and neutral charge directors, which may not disassociate or react with acids or bases to form charges, such as fluorosurfactants.

In some examples, the concentration of colorant particles in the electronic ink may range from about 0.5 to 20 percent by weight (wt %). In other examples, the concentration of the colorant particles in the electronic ink may range from about 1 to 10 wt %. In some examples, the concentration of surfactant, dispersant, or other additives together in the electronic ink may range from about 0.5 to 20 percent by weight (wt %). In other examples, the concentration of such additives together may range from about 1 to 10 wt %. In such examples, the carrier fluid makes up the balance of the ink.

Figure 2:
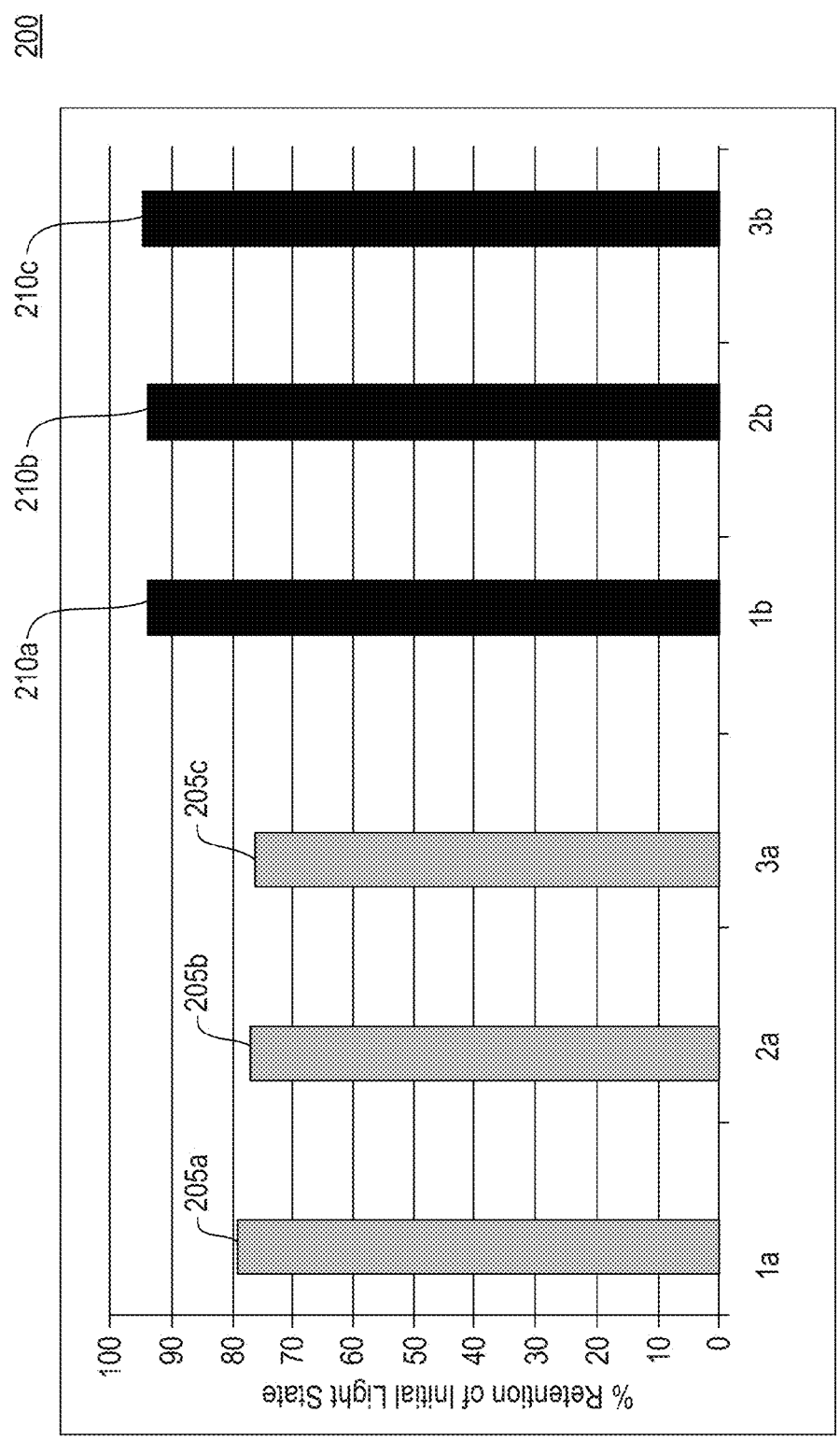
FIG. 2, on coordinates of percent retention and sample number, illustrates three trials measuring the percent retention of the initial light state of a device including an ink without the amine substituted surfactant disclosed herein and of a device including an ink with the amine substituted surfactant disclosed herein 30 seconds after the power source has been removed from the devices.

FIG. 2, on coordinates of percent retention and sample number, illustrates three trials 205a, 205b, 205c measuring the percent retention of the initial light state of a device including an ink without the amine substituted surfactant disclosed herein 30 seconds after the power source was removed from the device, and three trials 210a, 210b, 210c measuring the percent retention of the initial light state of a device including an ink with the amine substituted surfactant disclosed herein 30 seconds after the power source was removed from the device. As seen in graph 200 the trials using devices loaded with ink with the amine substituted surfactant 210a, 210b, 210c had a higher percent retention of the initial light state after removal from the power source than the trials loaded with ink without the amine substituted surfactant 205a, 205b, 205c. This result suggests that inks including the amine substituted surfactant disclosed herein have better multi-stability properties than inks without the amine substituted surfactant disclosed herein.

Figure 3:
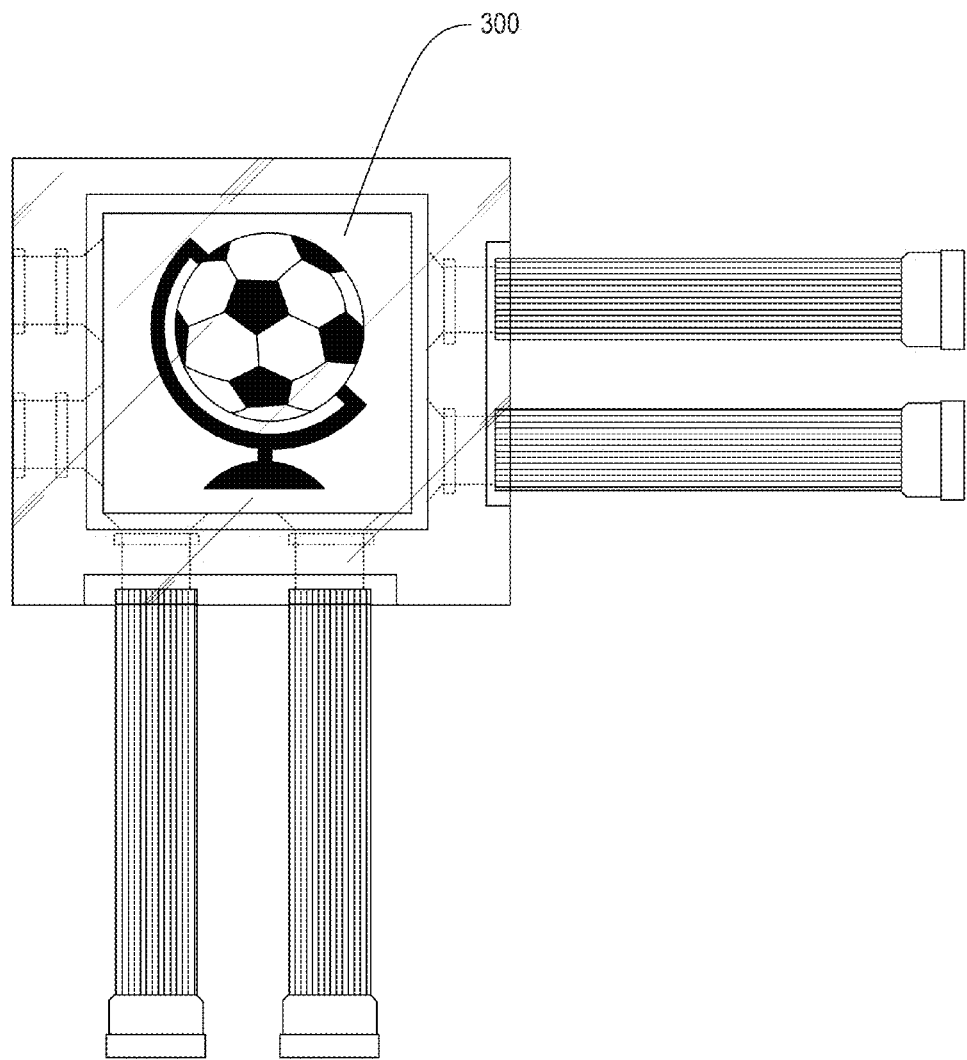
FIG. 3 is a depiction of an image displayed in an electrokinetic device using an electronic ink including the amine substituted surfactant disclosed herein 40 minutes after the electrophoretic device has been removed from the power source.

FIG. 3 is a depiction of an image displayed in an electrokinetic device using an electronic ink including the amine substituted surfactant disclosed herein 40 minutes after the electrokinetic device has been removed from a power source. As seen in image 300, 40 minutes after the electrokinetic device has been removed from the power source, the image is still clearly visible, suggesting that the electronic ink including the amine substituted surfactant disclosed herein has at least bi-stability properties or in other words, is capable of maintaining both the clear state and a single colored state after removal from a power source.

Figure 4A:
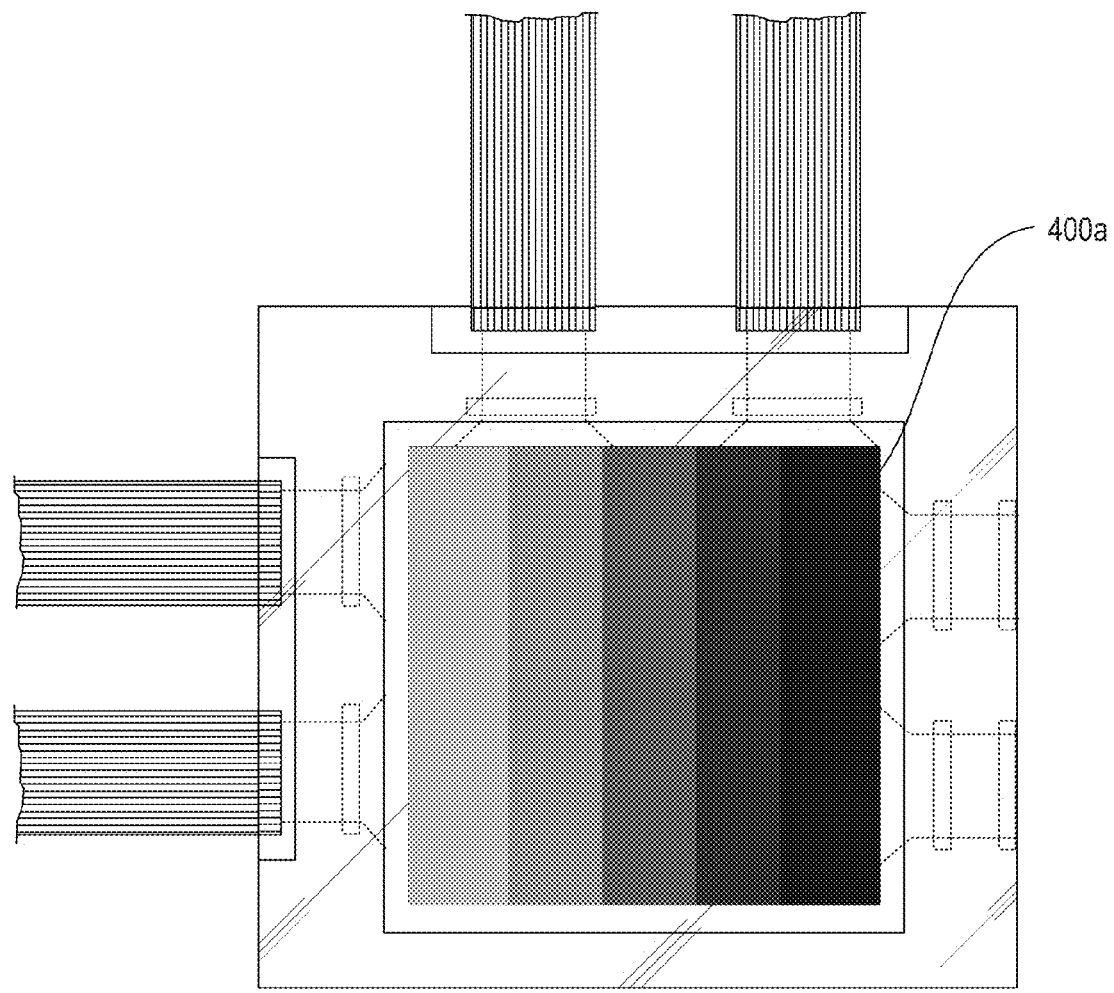
FIG. 4A is a depiction of an image displayed in an electrokinetic device using an electronic ink including the amine substituted surfactant disclosed herein and connected to a power source.
Figure 4B:
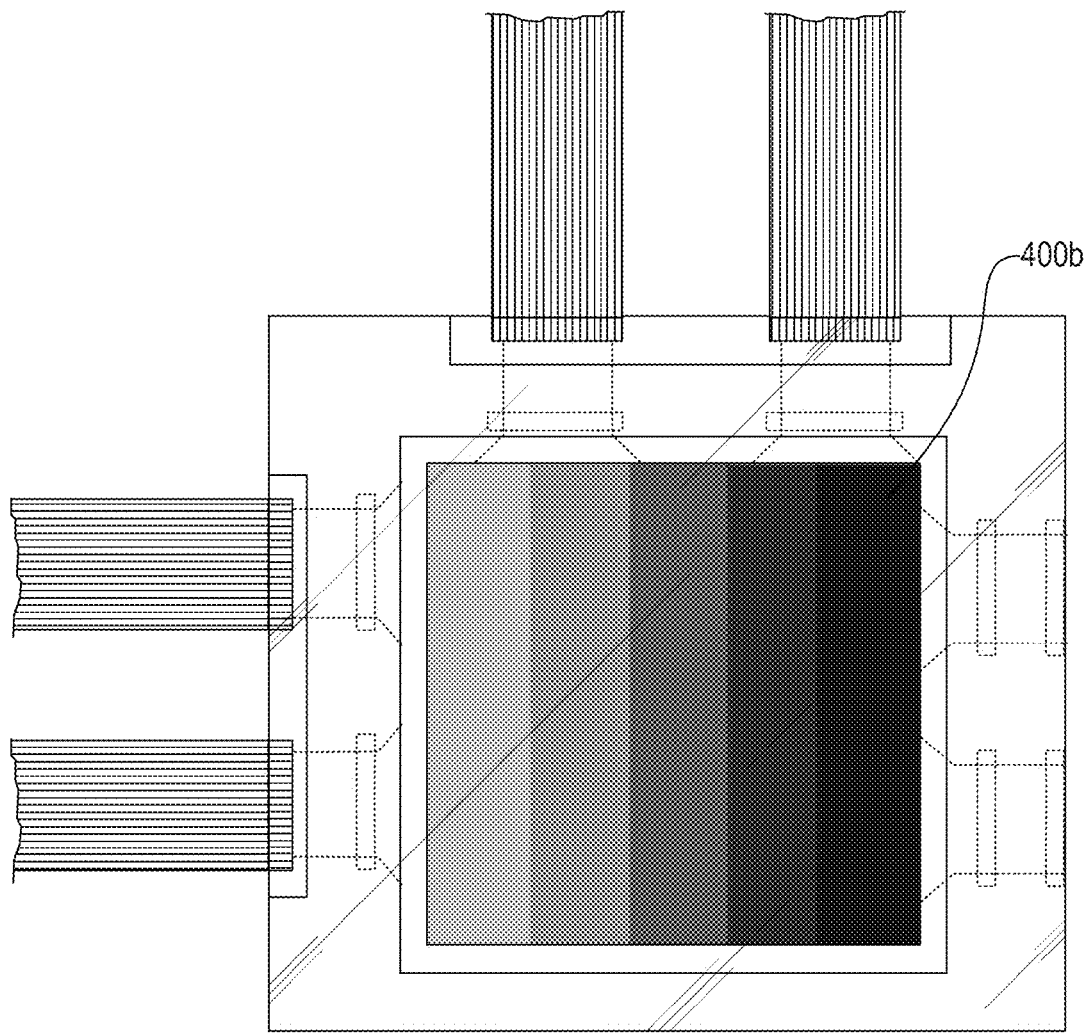
FIG. 4B is a depiction of an image displayed in the electrokinetic device of FIG. 4A 15 hours after the electrokinetic device has been disconnected from a power source.

FIG. 4A is a depiction of an image 400 displayed in an electrokinetic device using an electronic ink including the amine substituted surfactant disclosed herein and connected to a power source, and FIG. 4B is a depiction of an image 405 displayed in the same electrokinetic device 15 hours after the electrokinetic device has been disconnected from a power source. As seen in the image 15 hours after the electrokinetic device has been removed from a power source 405, the image of the color gradient is still clearly visible, suggesting that the electronic ink has multi-stability properties or in other words, is capable of maintaining multiple colored states after removal from a power source.

It should be understood that the foregoing multi-stable electronic inks including linear, branched, or cyclic hydrocarbon substituted tertiary amines have been described with specific application to electrokinetic devices. However, such inks may find use in electrophoretic devices as well.

EXAMPLES

Example 1

Example General Method for Synthesis of Alkyl or Cycloalkyl Substituted Polyaliphatic Amines (9) and (10)

First, a mixture of polyisobutylene succinic anhydride (5 g, 5 mmol), linear, branched, or cyclic hydrocarbon substituted tertiary amine (5 mmol) in 60 mL of xylenes (including 1,2-xylene, 1,3-xylene, and 1,4-xylene) is refluxed for 8 hours. Then, the solution is cooled down to room temperature and is washed with 10 mL of a 0.5M sodium bicarbonate (NaHCO$_3$) solution three times, 10 mL of a 0.5 M hydrochloric acid (HCl) solution three times, and 10 mL of deionized water three times. Afterwards, the organic layer is dried using magnesium sulfate (MgSO$_4$), and the remaining solvent is dried by rotary evaporator, resulting in a brown colored viscous liquid. Finally, the liquid is further purified by column chromatography, eluting first with hexane and ethyl acetate (10:1), then with tetrahydrofuran (THF), and lastly with chloroform (CHCl$_3$) and methanol (MeOH) (98:2).

Example 2

Example General Method for Synthesis of Alkyl or Cycloalkyl Tertiary Amine Terminated Polyethylene Glycols (20) and (21)

First, a mixture of polyisobutylene succinic anhydride (5 g, 5 mmol), linear, branched, or cyclic hydrocarbon substituted tertiary amines terminated polyethylene glycols (5 mmol) in 60 mL of xylenes (including 1,2-xylene, 1,3-xylene, and 1,4-xylene) is refluxed for 8 hours. Then, the solution is cooled down to room temperature and is washed with 10 mL of a 0.5M sodium bicarbonate (NaHCO$_3$) solution three times, 10 mL of a 0.5 M hydrochloric acid (HCl) solution three times, and 10 mL of deionized water three times. Afterwards, the organic layer is dried using magnesium sulfate (MgSO$_4$), and the remaining solvent is dried by rotary evaporator, resulting in a brown colored viscous liquid. Finally, the liquid is further purified by column chromatography, eluting first with hexane and ethyl acetate (10:1), then with tetrahydrofuran (THF), and lastly with chloroform (CHCl$_3$) and methanol (MeOH) (98:2).

Example 3

Example General Method for Synthesis of Alkyl or Cycloalkyl Tertiary Amines Terminated Alkanes (31) and (32)

First, a mixture of polyisobutylene succinic anhydride (5 g, 5 mmol), linear, branched, or cyclic hydrocarbon substituted tertiary amines terminated alkanes (5 mmol) in 60 mL of xylenes (including 1,2-xylene, 1,3-xylene, and 1,4-xylene) is refluxed for 8 hours. Then, the solution is cooled down to room temperature and is washed with 10 mL of a 0.5M sodium bicarbonate (NaHCO$_3$) solution three times, 10 mL of a 0.5 M hydrochloric acid (HCl) solution three times, and 10 mL of deionized water three times. Afterwards, the organic layer is dried using magnesium sulfate (MgSO$_4$), and the remaining solvent is dried by rotary evaporator, resulting in a brown colored viscous liquid. Finally, the liquid is further purified by column chromatography, eluting first with hexane and ethyl acetate (10:1), then with tetrahydrofuran (THF), and lastly with chloroform (CHCl$_3$) and methanol (MeOH) (98:2).

Example 4

Example Method for the Synthesis of Diethyl Substituted Polyaliphatic Amines (12)

First, a mixture of polyisobutylene succinic anhydride (5 g, 5 mmol), diethylenetriamine (0.58 g, 5 mmol) in 60 mL of xylenes (including 1,2-xylene, 1,3-xylene, and 1,4-xylene) was refluxed for 8 hours. Then, the solution was cooled down to room temperature and was washed with 10 mL of a 0.5M sodium bicarbonate (NaHCO$_3$) solution three times, 10 mL of a 0.5 M hydrochloric acid (HCl) solution three times, and 10 mL of deionized water three times. Afterwards, the organic layer was dried using magnesium sulfate (MgSO$_4$), and the remaining solvent was dried by rotary evaporator, resulting in a 60% yield of product as a brown colored viscous liquid. Finally, the liquid was further purified by column chromatography, eluting first with hexane and ethyl acetate (10:1), then with tetrahydrofuran (THF), and lastly with chloroform, (CHCl$_3$) and methanol (MeOH) (98:2).

What is claimed is:

1. A compound having the general structure:

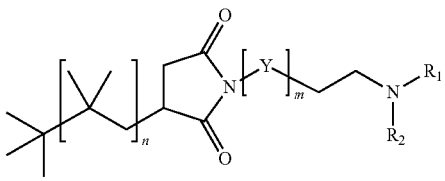

wherein Y is selected from the group consisting of hydrocarbons, hydrocarbons including nitrogen in the carbon backbone, and hydrocarbons including oxygen in the carbon backbone; wherein $R_1$ and $R_2$ are each independently selected from the group consisting of hydrogen, linear hydrocarbons, branched hydrocarbons, and cyclic hydrocarbons and wherein $R_1$ and $R_2$ are not both hydrogen; wherein m is an integer between 1 and 50, inclusive; and wherein n is an integer between 1 and 10,000, inclusive; or the general structure:

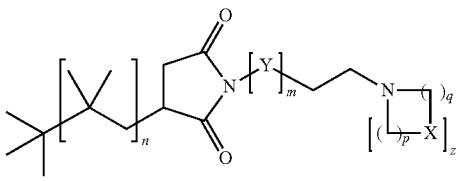

wherein Y is selected from the group consisting of hydrocarbons, hydrocarbons including nitrogen in the carbon backbone, and hydrocarbons including oxygen in the carbon backbone; wherein X is selected from the group consisting of CH$_2$, O, N—R$_3$, S, and nothing, wherein R$_3$ is selected from the group consisting of hydrogen, branched hydrocarbons, linear hydrocarbons, and cyclic hydrocarbons; wherein m is an integer between 1 and 50, inclusive; wherein n is an integer between 1 and 10,000, inclusive; and wherein p, q, and z are each independently an integer greater than 0.

2. The compound of claim 1 wherein Y is selected from the group consisting of aliphatic amines including between 1 and 50 carbons inclusive, glycols including between 1 and 50 carbons inclusive, alkyls including between 1 and 50 carbons inclusive, alkenyls including between 1 and 50 carbons inclusive, aryls including between 1 and 50 carbons inclusive, arylalkyls including between 1 and 50 carbons inclusive, and cycloalkanealkyls including between 1 and 50 carbons inclusive.

3. The compound of claim 1 wherein one of Y, $R_1$, and $R_2$ may be the same or may be different from another one of Y, $R_1$, and $R_2$, and wherein m and n may be the same or may be different from one another; or wherein one of m, n, p, q, and z may be the same or may be different from another one of m, n, p, q, and z.

4. An electronic ink including:
a non-polar carrier fluid;
a colorant particle; and
a compound having the general structure:

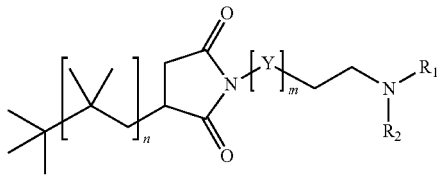

wherein Y is selected from the group consisting of hydrocarbons, hydrocarbons including nitrogen in the carbon backbone, and hydrocarbons including oxygen in the carbon backbone; wherein $R_1$ and $R_2$ are each independently selected from the group consisting of hydrogen, linear hydrocarbons, branched hydrocarbons, and cyclic hydrocarbons and wherein $R_1$ and $R_2$ are not both hydrogen; wherein m is an integer between 1 and 50, inclusive; and wherein n is an integer between 1 and 10,000, inclusive; or the general structure:

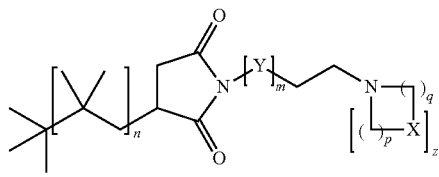

wherein Y is selected from the group consisting of hydrocarbons, hydrocarbons including nitrogen in the carbon backbone, and hydrocarbons including oxygen in the carbon backbone; wherein X is selected from the group consisting of $CH_2$, O, N—$R_3$, S, and nothing, wherein $R_3$ is selected from the group consisting of hydrogen, branched hydrocarbons, linear hydrocarbons, and cyclic hydrocarbons; wherein m is an integer between 1 and 50, inclusive; wherein n is an integer between 1 and 10,000, inclusive; and wherein p, q, and z are each independently an integer greater than 0.

5. The electronic ink of claim 4 wherein Y is selected from the group consisting of aliphatic amines including between 1 and 50 carbons inclusive, glycols including between 1 and 50 carbons inclusive, alkyls including between 1 and 50 carbons inclusive, alkenyls including between 1 and 50 carbons inclusive, aryls including between 1 and 50 carbons inclusive, arylalkyls including between 1 and 50 carbons inclusive, and cycloalkanealkyls including between 1 and 50 carbons inclusive.

6. The electronic ink of claim 4 wherein the non-polar carrier fluid is a non-polar solvent selected from the group consisting of hydrocarbons, halogenated hydrocarbons, partially halogenated hydrocarbons, siloxanes, and combinations thereof.

7. The electronic ink of claim 4 wherein the non-polar carrier fluid is a non-polar solvent selected from the group consisting of perchloroethylene, cyclohexane, dodecane, cyclopentasiloxane, cyclohexasiloxane, cyclooctamethylsiloxane, isoparaffinic fluids, mineral oil, and combinations thereof.

8. The electronic ink of claim 4 wherein the colorant particle is selected from the group consisting of black pigment particles, yellow pigment particles, magenta pigment particles, red pigment particles, violet pigment particles, cyan pigment particles, blue pigment particles, green pigment particles, orange pigment particles, brown pigment particles, and white pigment particles.

9. The electronic ink of claim 4 wherein the colorant particle is a colored polymeric particle having a size ranging from 10 nm to 10 μm.

10. The electronic ink of claim 4 further including a charge director, wherein the charge director is a small molecule or polymer that is capable of forming reverse micelles in the non-polar carrier fluid.

11. In combination, an electronic display and an electronic ink, wherein the electronic display includes:
a first electrode;
a second electrode; and
a display cell having a recess defined by a dielectric material, the first electrode, and the second electrode, the display cell containing the electronic ink wherein the electronic ink includes:
a non-polar carrier fluid;
a colorant particle; and
a compound having the general structure:

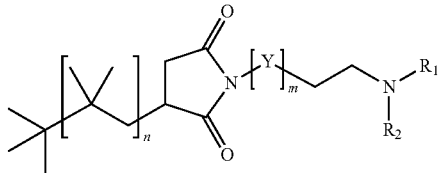

wherein Y is selected from the group consisting of hydrocarbons, hydrocarbons including nitrogen in the carbon backbone, and hydrocarbons including oxygen in the carbon backbone; wherein $R_1$ and $R_2$ are each independently selected from the group consisting of hydrogen, linear hydrocarbons, branched hydrocarbons, and cyclic hydrocarbons and wherein $R_1$ and $R_2$ are not both hydrogen: wherein m is an integer between 0 and 50, inclusive; and wherein n is an integer between 1 and 10,000, inclusive; or the general structure:

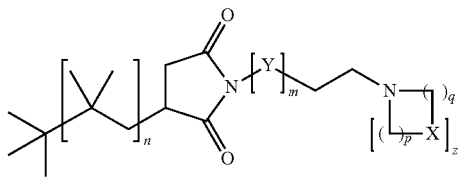

wherein Y is selected from the group consisting of hydrocarbons, hydrocarbons including nitrogen in the carbon backbone, and hydrocarbons including oxygen in the carbon backbone; wherein X is selected from the group consisting of $CH_2$, O, N—$R_3$, S, and nothing, wherein $R_3$ is selected from the group consisting of hydrogen, branched hydrocarbons, linear hydrocarbons, and cyclic hydrocarbons; wherein m is an integer between 1 and 50, inclusive; wherein n is an integer between 1 and 10,000, inclusive; and wherein p, q, and z are each independently an integer greater than 0.

12. The combination of claim 11 wherein the electronic display includes a plurality of display cells in a stacked configuration, associated first electrodes and second electrodes, and a plurality of electronic inks of different colors, each display cell containing an electronic ink of a different color.

13. The combination of claim 11 wherein the non-polar carrier fluid is a non-polar solvent selected from the group consisting of hydrocarbons, halogenated hydrocarbons, partially halogenated hydrocarbons, siloxanes, and combinations thereof.

14. The combination of claim 11 wherein the colorant particle has a size ranging from 10 nm to 10 µm and is selected from the group consisting of black pigment particles, yellow pigment particles, magenta pigment particles, red pigment particles, violet pigment particles, cyan pigment particles, blue pigment particles, green pigment particles, orange pigment particles, brown pigment particles, and white pigment particles.

15. The combination of claim 11 wherein the electronic ink further includes a charge director, wherein the charge director is a small molecule or polymer that is capable of forming reverse micelles in the non-polar carrier fluid.

\* \* \* \* \*